United States Patent [19]

Aihara et al.

[11] Patent Number: 5,116,877
[45] Date of Patent: May 26, 1992

[54] PHARMACEUTICAL USE FOR CINNAMAMIDE DERIVATIVES

[75] Inventors: Hironaka Aihara; Michio Kurachi, both of Kitamoto; Kazuyuki Tomisawa, Saitama, all of Japan

[73] Assignee: Taisho Pharmaceutical Co., Ltd., Japan

[21] Appl. No.: 471,596

[22] Filed: Jan. 29, 1990

[30] Foreign Application Priority Data

Feb. 2, 1989 [JP] Japan .................................. 1-024159

[51] Int. Cl.$^5$ ............................................ A01N 37/18
[52] U.S. Cl. .................................... 514/617; 514/613; 514/615; 514/620
[58] Field of Search ......................... 514/617, 615, 620

[56] References Cited

U.S. PATENT DOCUMENTS

| | | | |
|---|---|---|---|
| 3,780,102 | 12/1973 | Bayssat et al. | 260/558 R |
| 4,190,647 | 2/1980 | Grivsky | 424/324 |
| 4,309,444 | 1/1982 | Grivsky | 424/324 |

FOREIGN PATENT DOCUMENTS

| | | |
|---|---|---|
| 6489 | 10/1967 | France . |
| 2340303 | 2/1977 | France . |
| 1131727 | 4/1967 | United Kingdom . |
| 1131728 | 4/1967 | United Kingdom . |

OTHER PUBLICATIONS

Dialog Information Services, file 5: Biosis 66-90, accession No. 0018138375 "Cinflumide a chemically novel centrally acting skeletal muscle relaxant".
J. Med. Chem., vol. 9, No. 5, May 1966, pp. 675-681; E. Van Heyningen et al. "N-monoalkyl-beta-alkylcinnamamides as sedatives".
Arzneim-Forsch./Drugs Red., vol. 27, No. 8, Aug. 1977, pp. 1612-1615 "Elektro-myographische Untersuchungen zur Wirkung des Zimtsaurederivats ... ".
E. Van Heymingen, et al., J. Med. Chem., vol. 9 (No. 5) pp. 675-681 (May 1966).

Primary Examiner—Leonard Schenkman
Assistant Examiner—T. J. Criares
Attorney, Agent, or Firm—Lorusso & Loud

[57] ABSTRACT

A cinnamamide derivative represented by the formula

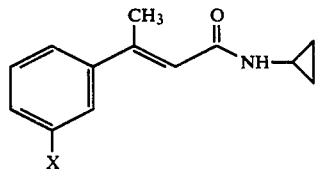

wherein X is a halogen atom is useful as a muscle relaxant.

4 Claims, No Drawings

PHARMACEUTICAL USE FOR CINNAMAMIDE DERIVATIVES

BACKGROUND OF THE INVENTION (1) Field of the Invention

The present invention relates to a new pharmaceutical use for cinnamamide derivatives and more particularly to use of cinnamamide derivatives for centrally relaxing muscle tone.

(2) Prior Art

The cinnamamide derivatives of the present invention have not been reported except that (E)-N-cyclopropyl-3-(3-chlorophenyl)-2-butenamide has disclosed as showing sedative or taming action in J. Med. Chem., vol. 9 (No. 5), page 675–681 (1966). The drugs showing the sedative or taming action lower the abnormally high psychic state of the upper central nervous system or depress the hyperemotion. On the contrary, the muscle relaxant normalizes the disorder of motor nervous system. Therefore, these two pharmacological actions are different apparently each other. Accordingly, it has heretofore been realized that the muscle relaxant is different from the sedative agent in the object of the use.

Furthermore, there are known other cinnamamide derivatives having the muscle relaxing activity, of which a typical compound is cinflumide that has the most preferred effect (Japanese Patent Publication No. 60-56700).

As a result of the earnest researches, the present inventors have found some cinnamamide derivatives to have much stronger and prolonged centrally-acting muscle relaxation activity, and have accomplished the present invention.

SUMMARY OF THE INVENTION

An object of the present invention is to provide a method for relaxing muscle tone which comprises administering to a patient a pharmaceutically effective amount of a cinnamamide derivative represented by the formula

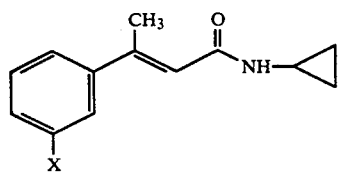

where X is a halogen atom.

In one aspect of the present invention, there is provided use of a cinnamamide derivative of Formula I for the manufacture of a pharmaceutical composition for relaxing muscle tone.

In further another aspect of the present invention, there is provided a pharmaceutical composition for relaxing muscle tone which comprises a cinnamamide derivative represented by Formula I as active ingredient and a pharmaceutically acceptable carrier.

DETAILED DESCRIPTION OF THE INVENTION

In Formula I, the halogen atom refers to a fluorine, chlorine, bromine or iodide atom, and preferably a fluorine or chlorine atom.

The compound of Formula I can be prepared, for example, as follows: a (E)-3-(3-halogenophenyl)-2-butenoic acid well-known is first reacted with an ordinary halogenating agent (e.g., thionyl chloride, phosphorus pentachloride, phosphorus oxychloride, oxalyl chloride, thionyl bromide or phosphorus tribromide) to give an acid halide of the formula

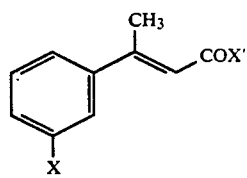

wherein X is as defined above, and X' is a halogen atom. Although the halogenating agent itself in this reaction can be a solvent, the reaction is also achieved in an inert-solvent (e.g., benzene, toluene, tetrahydrofuran, ether, methylene chloride or chloroform) with stirring at room temperature to the reflux temperature of the solvent for 30 minutes to 5 hours. A catalyst is not necessarily used, but acceleration of the reaction can be achieved by the addition of a catalystic amount to an equimolar amount of a catalyst such as pyridine, triethylamine or N,N-dimethylformamide.

The compound of Formula II dissolved in the same inert-solvent as described above is then reacted with cyclopropylamine to give the compound of Formula I. In order to eliminate the halogenated hydrogen which forms in the reaction, it is preferable to use more than two molar equivalents of cyclopropylamine, or it is preferable to coexist a tert-amine such as pyridine or triethylamine. The reaction is carried out at from −30° to 50° C., and finished by 1 to 24 hours.

Alternatively, a (E)-3-(3-halogenophenyl)-2-butenoic acid is reacted with an alkyl halogenocarbonate (e.g., methyl chlorocarbonate, ethyl chlorocarbonate and isobutyl chlorocarbonate) in the presence of a base (e.g., triethylamine, diisopropylethylamine and N-methylmorpholine) in the same inert-solvent as described above at −30° to 30° C. for 0.2 to 3 hours to give a mixed acid anhydride represented by the formula

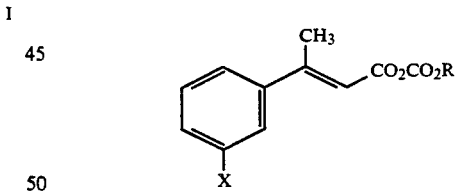

wherein X is as defined above and R is an alkyl group having 1 to 7 carbon atoms, which is then in the reaction solution, without isolation, reacted with cyclopropylamine at the same temperature to give the compound of Formula I.

The compounds of Formula I exhibit remarkable muscle relaxant and rigidity mitigation activity. On the other hand, their sedative activity is weak at the dose effective to relax muscle tone. Accordingly, these compounds are useful as the therapeutic agents of the disorder of motor nervous system such as dolorous muscle spasm (e.g., low-back pain and back pain, and herniated disc of the spine) or spastic paralysis such as the cerebral injuries. For these purposes, the compound of Formula I is mixed with suitable pharmaceutically acceptable carriers for solid or liquid form to give the pharmaceutical preparation for oral or parenteral administration. Examples of the pharmaceutical preparation are solid forms such as tablets, pills, capsules and granules, liquid forms such as injectional solutions, syrups and emulsions, and external forms such as ointments and suppositories, all of which can be prepared according to conventional pharmaceutical practices. The carriers in the above-mentioned preparations can include ordinary additives such as auxiliaries, stabilizers, wetting agents and emulsifiers. For example, there can be used solublizers (e.g., injectional distilled water, physiological saline solution and Ringer's solution) and preservers (e.g., methyl p-oxybenzoate and propyl p-oxybenzoate) for injectional solutions; and used sorbitol syrup, methylcellulose, glucose, sucrose syrup, hydroxyethylcellulose, food oil, glycerin, ethanol, water, emulsifers (e.g., gum arabic and lecithin) and detergents (e.g., Tween or Span) for syrups and emulsions. For the solid forms, there can be used excipients (e.g., lactose, corn starch and mannitol), lubricants (calcium phosphate, magnesium stearate and tulc), binders (e.g., sodium carboxymethylcellulose and hydroxypropylcellulose), disintegraters (e.g., crystal cellulose, calcium carboxymethylcellulose) and fluid accelerators (e.g., light silicic anhydride).

The dosage of the compound of Formula I depends on the age of the patient, the kind and conditions of the disease, but usually it is from 5 to 1000 mg in single or several divided doses per adult per day.

Then, the experiments are illustrated below in order to show the effects of the compounds of Formula I.

Experiment 1 [Inhibition test of the mesocephalous decerebrate rididity]

The rigidity animals were prepared according to the method of Ono et al [Gen. Pharm., vol. 18, page 57-59 (1987)].

Four male Wistar rats weighing 250 to 350 g were used for each group. The animals were anesthetized with ethyl ether and fixed on a brain stereotaxic apparatus to break the midbrain bilaterally (APO, V-3, L ±1.5). The advanced rigidity occurred in the hind limb with awaking from the ethyl ether anesthesia. The test drugs [A; (E)-N-cyclopropyl-3-(3-chlorophenyl)-2-butenamide, B; (E)-N-cyclopropyl-3-(3-fluorophenyl)-2-butenamide and C; cinflumide] dissolved in propylene glycol were each administered intravenously in the amount of 5 mg/kg or 10 mg/kg (0.1 ml per 100 g of rat), and these test drugs suspended in 0.4% aqueous carboxymethylcellulose solution were each administered intraduodenally in the amount of 50 mg/kg (0.1 ml per 100 g of rat) to determine the inhibition time of the rigidity.

Results are shown in Table 1.

TABLE 1

| Drug | Dose (mg/kg i.v.) | | Dose (mg/kg i.d.) |
|---|---|---|---|
|  | 5 | 10 | 50 |
| A | 13 | 37* | 36* |
| B | 6 | 12 | 53 |
| C | 0 | 3 | 0 |

*The values show the length of time (minutes) during which the inhibition action occurs.

Experiment 2 [Inhibition of Anemic Decerebrate rigidity]

The rigidity animals were prepared according to the method of Fukuda et al [Japan J. Pharmacol., vol. 24, page 810-813 (1974)].

Four male Wistar rats weighing 250 to 350 g were used for each group.

The animals were anesthetized with ethyl ether and carotid artery was ligated bilaterally: A round hole was digged in the suboccipital skeleton and the basal artery was coagulated using a bipolar electrocoagulator. The advanced rigidity occurred on the fore limb with awaking from the ethyl ether anesthesia. The drugs [A; (E)-N-cyclopropyl-3-(3-chlorophenyl)-2-butenamide, B; (E)-N-cyclopropyl-3-(3-fluorophenyl)-2-butenamide, and C; cinflumide] dissolved in polyethylene glycol 400 were each administered intravenously in the amount of 5 mg/kg or 10 mg/kg (0.1 ml per 100 g of rat) to determine the inhibition time of the rigidity.

Results are shown in Table 2.

TABLE 2

| Drug | Dose (mg/kg i.v.) | |
|---|---|---|
|  | 5 | 10 |
| A | 9 | 13* |
| B | 8 | 12 |
| C | — | 8 |

*The values show the length of time (minutes) during which the inhibition occurs.

Experiment 3 [Straub tail reaction]

Test was carried out according to the method of Ellis et al [Neuropharmacology, vol. 13, page 211 to (1974)].

Six male ICR mice weighing 20-30 g were used as the animals for each group. The drugs [A; (E)-N-cyclopropyl-3-(3-chlorophenyl)-2-butenamide, and C; cinflumide] suspended in 0.4% aqueous carboxymethylcellulose solution were each administered orally to the animals in the amounts of 50, 70.7, 100 and 140 mg/kg (0.1 ml per 10 g of mouse). After 15 minutes, 15 mg/kg of morphine hydrochloride were administered subcutaneously. After 30 minutes, the tail-raising reaction was determined. The muscle relaxation activity was judged as positive in case where the drug produces the value of less than 45 degrees of the tail-raising's angle, and the inhibition rate was culculated.

Results are shown in Table 3.

TABLE 3

| Drug | Dose (mg/kg i.v.) | | | |
|---|---|---|---|---|
|  | 50 | 70.7 | 100 | 140 |
| A | 40 | 40 | 100 | 100* |
| C | 0 | 20 | 80 | 100 |

*The values show the inhibition rate (%).

Experiment 4 [Spontaneous motor activity test]

Six male ICR mice weighing 20-30 g were used as the test animals for each group. The test drugs [A: (E)-N-cyclopropyl-3-(3 chlorophenyl)-2-butenamide and B: (E)-N-cyclopropyl-3-(3-fluorophenyl)-2-butenamide] suspended in 0.4% aqueous carboxymethylcellulose solution were each administered orally to mice in the amounts of 50, 70.7 and 100 mg/kg (0.1 ml per 10 g of mouse). The control group were administered with 0.4% aqueous carboxymethylcellulose solution only.

After 15 minute, mice were placed in ANIMEX apparatus (manufactured by Muromachi Kikai K.K.) to determine the spontaneous moter activity for 30 minutes Results after 30 minutes of the administration are shown in Table 4.

From the results the group treated with the test drugs was found not to have substantial inhibition activity when compared with the control group.

TABLE 4

| Drug | Dose (mg/kg p.o.) | Spontaneous motor activity (Counts/30 minutes) |
|---|---|---|
| A | 50 | 1736.0 ± 366.6 |
|   | 70.7 | 1570.2 ± 326.9 |
|   | Control | 2116.0 ± 256.6 |
| B | 70.7 | 2264.2 ± 506.0 |
|   | 100 | 1667.8 ± 152.4 |
|   | Control | 2128.7 ± 228.0 |

Experiment 5 [Acute toxicity test]

Ten male ICR mice weighing 25 to 34 g were used. (E)-N-cyclopropyl-3-(3-chlorophenyl)-2-butenamide suspended in 0.4% aqueous carboxymethylcellulose solution was each administered orally to mice in the amount of 0.1 ml per 10 g of mice. The survivals were observed for 7 days after administration, but no death occurred in case of the dose of 1 g/kg. The $LD_{50}$ values were more than 1 g/kg p.o.

The present invention is illustrated by the following examples in more detail, and Compounds 1 and 2 in Examples 1 to 5 mean (E)-N-cyclopropyl-3-(3-chlorophenyl)-2-butenamide and (E)-N-cyclopropyl-3-(3-fluorophenyl)-2-butenamide, respectively.

EXAMPLE 1 (Tablets)

| Compound 1 | 600 g |
|---|---|
| Crystal cellulose | 120 g |
| Corn starch | 125 g |
| Hydroxypropylcellulose | 45 g |
| Magnesium stearate | 10 g |
| Total | 900 g |

The above components were mixed according to an ordinary manner and tableted to give 9 mm diameter tablets weighing 300 mg.

EXAMPLE 2

| Compound 2 | 600 g |
|---|---|
| Crystal cellulose | 150 g |
| Corn starch | 140 g |
| Magnesium stearate | 10 g |
| Total | 900 g |

The above components were mixed according to an ordinary manner, and each 300 mg of the mixture was filled into a No. 1 cupsule.

EXAMPLE 3 (Granules)

| Compound 1 | 200 g |
|---|---|
| Mannitol | 300 g |
| Corn starch | 450 g |
| Magnesium stearate | 10 g |
| Hydroxypropylcellulose | 50 g |
| Total | 1010 g |

Granules were prepared from the above components by a wet granulation method.

EXAMPLE 4 (Powders)

| Compound 1 | 200 g |
|---|---|
| Lactose | 800 g |
| Total | 1000 g |

The above components were mixed uniformly according to an ordinary manner to give powders, each 1000 mg of which were filled into a pack.

EXAMPLE 5

Fifty g of Compound 2 was dissolved in 1000 ml of distilled water for injection and filled into 2 ml ampules.

EXAMPLE 6

To a solution of 18.0 g of (E)-3-(3-fluorophenyl)-2-butenoic acid in 200 ml of benzene was added 14.5 ml of thionyl chloride, and the mixture was stirred at reflux under heating. The benzene and the excess amount of thionyl chloride were evaporated under reduced pressure, and the residue was concentrated to give 19 g of the crude acid chloride. To a solution of the crude chloride in 200 ml of toluene was added dropwise a solution of 15.2 ml of cyclopropylamine in 50 ml of toluene under ice-cooling with stirring, and the mixture was stirred at room temperature for 6 hours. The reaction solution was washed, in turn, with water, a saturated aqueous bicarbonate solution, dilute hydrochloride and water, and dried over magnesium sulfate. The toluene was evaporated under reduced pressure, and the residue was recrystallized from n-hexane-acetone to give 12.9 g of (E)-N-cyclopropyl-3-(3-fluorophenyl)-2-butenamide as colorless needles.

m.p. 119.0°–120 5° C.

EXAMPLE 7

To a solution of 18.0 g of (E)-3-(3-fluorophenyl)-2-butenoic acid in 200 ml of toluene was added 13.9 ml of triethylamine under cooling and a nitrogen atmosphere with stirring, followed by the addition of 13.0 ml of isobutyl chlorocarbonate, and then the solution was stirred at room temperature for 30 minutes. To the reaction solution cooled on ice was added dropwise 7.6 ml of cyclopropylamine with stirring, and the mixture was stirred at room temperature for 2 hours. Then, following a procedure similar to that of Example 6 to give 14.0 g of (E)-N-cyclopropyl-3-(3-fluorophenyl)-2-butenamide.

m.p. 119.0°–120.5° C.

Following a procedure similar to that of Example 7, there was obtained (E)-N-cyclopropyl-3-(3-bromopheyl)-2-butenamide.

m.p. 129.0°–131.5° C.

What is claimed is:

1. A method for relaxing muscle tone which comprises administering to a patient in need thereof 5–1000 mg per adult per day of a cinnamamide derivative represented by the formula

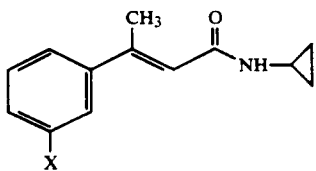

wherein X is fluorine or chlorine.

2. A method according to claim 1, wherein the cinnamamide derivative is (E)-N-cyclopropyl-3-(3-chlorophenyl)-2-butenamide.

3. A method according to claim 1, wherein the cinnamamide derivative is (E)-N-cyclopropyl-3-(3-fluorophenyl)-2-butenamide.

4. A method according to claim 1, wherein the cinnamamide derivative is administered in the form of tablet, pill, capsule, granule, injectional solution, syrup, emulsion, ointment or suppository.

* * * * *

UNITED STATES PATENT AND TRADEMARK OFFICE
CERTIFICATE OF CORRECTION

PATENT NO. : 5,116,877
DATED : May 26, 1992
INVENTOR(S) : Aihara, et al

It is certified that error appears in the above-identified patent and that said Letters Patent is hereby corrected as shown below:

Col. 3, line 35, delete "rididity" insert --rigidity--.

Col. 4, line 11, delete "digged" insert --dug--;

line 34, after "to" insert --214--;

line 47, delete "culculated" insert --calculated--.

Col. 5, line 3, delete "moter" insert --motor--;

line 47, "EXAMPLE 2" should read

--EXAMPLE 2 (CAPSULES)--; and line 58, delete "cupsule" insert --capsule--.

Signed and Sealed this

Tenth Day of August, 1993

Attest:

MICHAEL K. KIRK

Attesting Officer     Acting Commissioner of Patents and Trademarks

UNITED STATES PATENT AND TRADEMARK OFFICE
CERTIFICATE OF CORRECTION

PATENT NO. : 5,116,877

DATED : May 26, 1992

INVENTOR(S) : AIHARA et al

It is certified that error appears in the above-identified patent and that said Letters Patent is hereby corrected as shown below:

On the title page, item [75] Inventors, insert the name "Kazuya Kameo".

Signed and Sealed this

Twenty-first Day of September, 1993

*Attest:*

BRUCE LEHMAN

*Attesting Officer*     *Commissioner of Patents and Trademarks*